United States Patent
Mundt

(10) Patent No.: US 10,463,179 B1
(45) Date of Patent: Nov. 5, 2019

(54) BODY COMPRESSION SLEEPWEAR

(71) Applicant: Matthew J. Mundt, Brookfield, WI (US)

(72) Inventor: Matthew J. Mundt, Brookfield, WI (US)

( * ) Notice: Subject to any disclaimer, the term of this patent is extended or adjusted under 35 U.S.C. 154(b) by 0 days.

(21) Appl. No.: 16/297,768

(22) Filed: Mar. 11, 2019

(51) Int. Cl.
*A47G 9/08* (2006.01)
*A61M 21/02* (2006.01)
*A41B 13/06* (2006.01)
*A61M 21/00* (2006.01)

(52) U.S. Cl.
CPC .............. *A47G 9/08* (2013.01); *A41B 13/06* (2013.01); *A41B 13/065* (2013.01); *A47G 9/083* (2013.01); *A61M 21/02* (2013.01); *A61H 2201/165* (2013.01); *A61M 2021/0022* (2013.01)

(58) Field of Classification Search
CPC ............ A47G 9/00; A47G 9/08; A47G 9/083; A47G 9/086; A61M 21/02; A61M 2021/0022; A61H 2201/165; A41B 13/06; A41B 13/065
See application file for complete search history.

(56) References Cited

U.S. PATENT DOCUMENTS

| | | | | |
|---|---|---|---|---|
| 2,008,919 A * | 7/1935 | Milkes | .................. | A41B 13/06 2/69 |
| 2,242,130 A * | 5/1941 | Hutchison | .............. | A47G 9/066 2/69.5 |
| 2,431,603 A * | 11/1947 | Zito | ........................ | A41B 13/06 2/114 |
| 2,478,765 A * | 8/1949 | Kim | .......................... | A41D 7/00 126/204 |
| 2,707,988 A * | 5/1955 | Shaub | ..................... | B62B 9/142 2/69.5 |
| 3,597,764 A * | 8/1971 | Povey | ..................... | A41D 15/04 2/69.5 |
| 3,842,454 A * | 10/1974 | Young | ..................... | A47G 9/086 119/28.5 |
| 4,888,828 A | 12/1989 | Tatsuno | | |
| 4,894,878 A * | 1/1990 | Roach | ..................... | A47G 9/086 2/272 |
| 5,283,909 A * | 2/1994 | Hill | ......................... | A47G 9/066 2/22 |

(Continued)

FOREIGN PATENT DOCUMENTS

WO     WO-2007098558 A1 *    9/2007     .......... A41B 13/005

*Primary Examiner* — David R Hare
(74) *Attorney, Agent, or Firm* — Donald J. Ersler

(57) ABSTRACT

Body compression sleepwear preferably includes a body portion and a neck portion. The body portion includes a first body sheet and a second body sheet. An outer perimeter of the first and second body sheets are sewn to each other with the exception of a straight end. The neck portion includes a first neck sheet and a second neck sheet. Opposing ends of the first and second neck sheets are sewn to each other to form the neck portion and an entrance opening. The neck portion is sewn to the straight end. The material of the body portion and the neck portion is preferably fabricated from a combination Polyester and Lycra fabric. The size of the compressive sleepwear is smaller than the user to exert compressive force on the outer surface of the user. The user inserts their legs and arms through the neck portion and into the body pocket.

19 Claims, 5 Drawing Sheets

(56) References Cited

U.S. PATENT DOCUMENTS

| | | | | |
|---|---|---|---|---|
| 5,437,061 A * | 8/1995 | Kenner | ............... | A41D 3/08 |
| | | | | 2/69 |
| 5,515,559 A * | 5/1996 | Benson | ............ | A47G 9/1045 |
| | | | | 428/16 |
| 6,393,612 B1 * | 5/2002 | Thach | ............ | A41B 13/065 |
| | | | | 2/69.5 |
| 8,191,189 B1 * | 6/2012 | Spell | ............ | A47G 9/083 |
| | | | | 5/494 |
| 8,464,374 B1 * | 6/2013 | Thayer | ............ | A47G 9/08 |
| | | | | 2/69 |
| 8,607,364 B2 * | 12/2013 | Barski | ............ | A41B 13/06 |
| | | | | 2/111 |
| 8,622,943 B2 | 1/2014 | Ben-Nun | | |
| 10,104,916 B2 * | 10/2018 | Barski | ............ | A41B 13/06 |
| 2004/0237192 A1 * | 12/2004 | Holub | ............ | A47G 9/086 |
| | | | | 5/413 R |
| 2007/0061968 A1 * | 3/2007 | Fader | ............ | A47D 15/008 |
| | | | | 5/494 |
| 2007/0226903 A1 * | 10/2007 | Paul | ............ | A47G 9/086 |
| | | | | 5/413 R |
| 2009/0282599 A1 * | 11/2009 | Comerford | ......... | A41B 13/06 |
| | | | | 2/69.5 |
| 2010/0257654 A1 * | 10/2010 | Waters | ............ | A41B 13/06 |
| | | | | 2/69.5 |
| 2011/0107502 A1 | 5/2011 | Dalhausser et al. | | |
| 2013/0227786 A1 * | 9/2013 | Sack | ............ | A41B 13/06 |
| | | | | 5/494 |
| 2017/0065843 A1 | 3/2017 | Foster | | |
| 2018/0103689 A1 * | 4/2018 | DeLisa | ............ | A41B 13/06 |

\* cited by examiner

BODY COMPRESSION SLEEPWEAR

BACKGROUND OF THE INVENTION

1. Field of the Invention

The present invention relates generally to sleeping garments and more specifically to body compression sleepwear, which promotes restful sleep.

2. Discussion of the Prior Art

Weighted blankets are capable of applying compressive forces to a top and bottom of a user's body, but are also very heavy and expensive. The weighted blankets are not really machine washable and may overheat the user during use. There are also fabric bags, which a user may slip into, but do not provide compressive forces to the outside surface of the body. U.S. Pat. No. 8,622,943 to Ben-Nun discloses a compression bag. Patent publication no. 2017/0065843 to Foster discloses a restriction compression weighted therapy suit. Patent publication no. 2011/0107502 to Dalhausser et al. discloses training and recovery clothing and related methods. U.S. Pat. No. 4,888,828 to Tatsuno discloses a sleeping bag device.

Accordingly, there is a clearly felt need in the art for body compression sleepwear, which applies compressive forces to the outside surface of a user's body; replicates being tightly wrapped in a swaddling garment like a baby; is lightweight; promotes restful sleep; and promotes a side sleeping position.

SUMMARY OF THE INVENTION

The present invention provides body compression sleepwear, which applies compressive forces to the outside surface of a user's body. The body compression sleepwear preferably includes a body portion and a neck portion. The body portion includes a first body sheet and a second body sheet. The first and second body sheets include a substantially oval shape, terminated by a straight end. An outer perimeter of the first and second body sheets are sewn to each other with the exception of the straight end to form a body pocket. The neck portion includes a first neck sheet and a second neck sheet. The first and second neck sheets include a rectangular shape and are folded over to form a double wall. Opposing ends of the first and second neck sheets are sewn to each other to form the neck portion and an entrance opening. A bottom of the neck portion is sewn to the straight end. A length of the neck portion is preferably about 15 percent of a length of the body portion. A width of the neck portion is preferably about 60 percent of a width of the body portion. The material of the body portion and the neck portion is preferably fabricated from a combination Polyester and Lycra fabric for stretch and memory. The size of the compressive sleepwear is smaller than the user to exert compressive force on the outer surface of the body of the user. The user inserts their legs and arms through the neck portion and into the body pocket. A head of a user is retained outside the neck portion. The user may keep their arms inside the body portion or extend a portion of one or two arms outside the neck portion. It is preferable that the user at least partially bend their legs when in the body pocket, similar to a fetal position of a baby.

Accordingly, it is an object of the present invention to provide compression sleepwear, which applies compressive forces to the outside surface of a user's body.

It is further object of the present invention to provide body compression sleepwear, which replicates being tightly wrapped in a swaddling garment like a baby.

It is another object of the present invention to provide body compression sleepwear, which is lightweight.

It is yet a further object of the present invention to provide body compression sleepwear, which promotes restful sleep.

Finally, it is another object of the present invention to provide body compression sleepwear, which promotes a side sleeping position.

These and additional objects, advantages, features and benefits of the present invention will become apparent from the following specification.

DETAILED DESCRIPTION OF THE PREFERRED EMBODIMENTS

Figure 1:
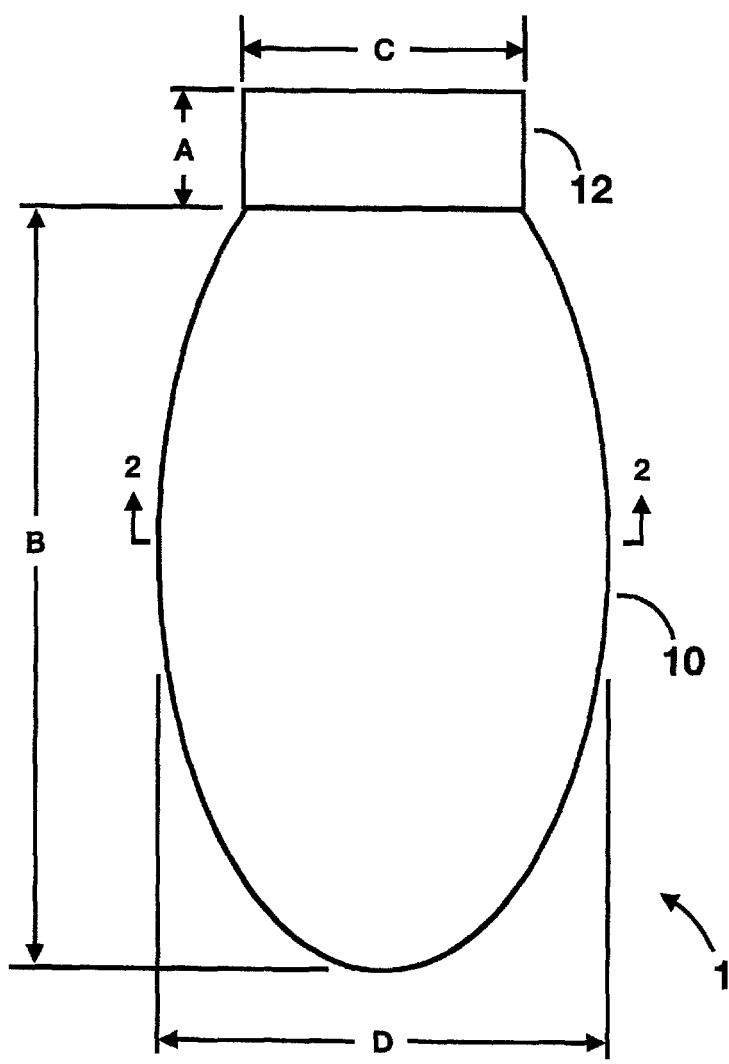
FIG. 1 is a front view of body compression sleepwear in accordance with the present invention.
Figure 2:
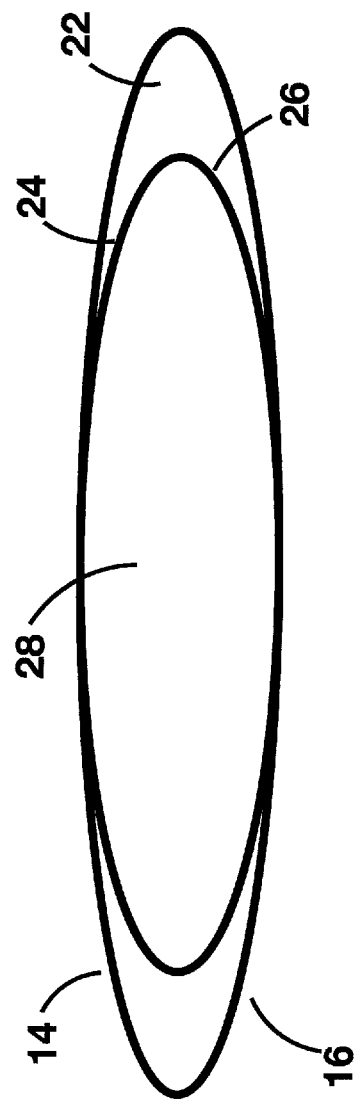
FIG. 2 is a cross sectional view of body compression sleepwear cut through FIG. 1 and a thickness slightly increased for illustration purposes in accordance with the present invention.
Figure 3:
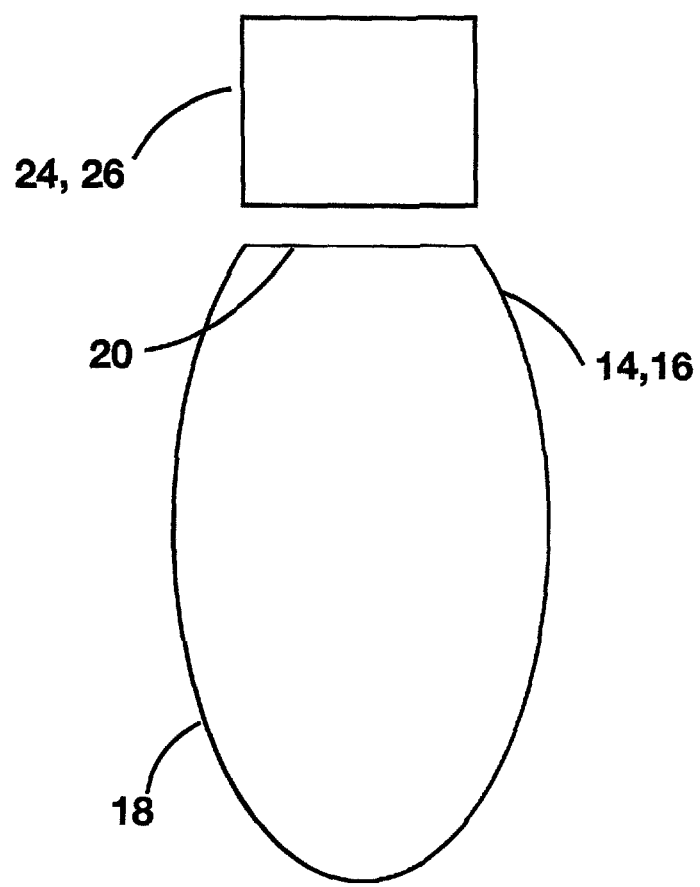
FIG. 3 is a front exploded view of a first or second neck sheet and a first or second body sheet, before sewing of body compression sleepwear in accordance with the present invention.

With reference now to the drawings, and particularly to FIG. 1, there is shown a front view of body compression sleepwear 1. The body compression sleepwear 1 preferably includes a body portion 10 and a neck portion 12. With reference to FIGS. 2-3, the body portion 10 includes a first body sheet 14 and a second body sheet 16. The first and second body sheets 14, 16 include a substantially oval shape 18, terminated by a straight end 20. An outer perimeter of the first and second body sheets 14, 16 are preferably sewn to each other, but could be attached to each other with any suitable process with the exception of the straight end to form a body pocket 22. The neck portion 12 includes a first neck sheet 24 and a second neck sheet 26. The first and second neck sheets 24, 26 include a rectangular shape and are folded over to form a double wall. Opposing ends of the first and second neck sheets 24, 26 are preferably sewn to each other, but could be attached to each other with any suitable process to form the neck portion 12 and an entrance opening 28. A bottom of the first neck sheet 14 is preferably sewn to the straight end 20 of the first body sheet 14, but could be attached to the straight end 20 with any suitable process and a bottom of the second neck sheet 16 is preferably sewn to the straight end 20 of the second body sheet 16.

Figure 3A:
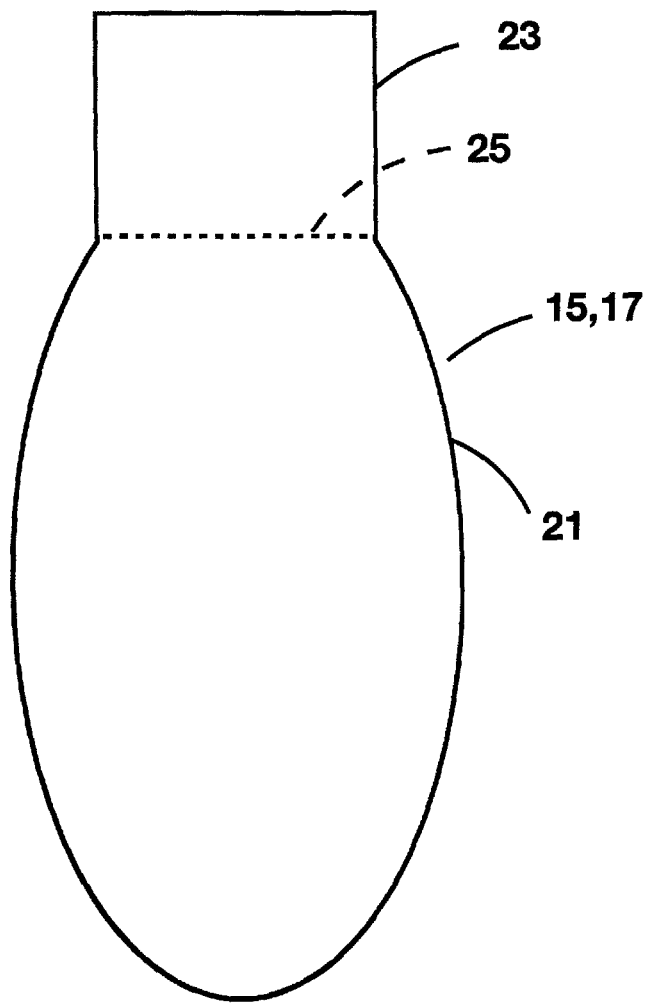
FIG. 3a is a front view of a first body side sheet or a second body side body sheet, before sewing of body compression sleepwear in accordance with the present invention.

With reference to FIG. 3a, a first or second body side sheet 15, 17 is shown. The first or second body side sheet 15, 17 include a body portion 21 and a neck portion 23 that extends from the body portion 21. The neck portion is folded over to line 25 to create a double wall. A perimeter of the first and second body side sheets 15, 17 are preferably sewn to each other, but could be attached to each other with any suitable process. A top of the neck portion 23 of the first and second body sides 15, 17 are sewn or attached to each other to form the entrance opening 28. A length "A" of the neck portion 12 is preferably about 15 percent of a length "B" of the body portion 10. A width "C" of the neck portion 12 is preferably about 60 percent of a width "D" of the body portion 10. The material of the body portion 10 and the neck portion 12 is preferably fabricated from a combination Polyester and Lycra fabric. The preferable percentage of Lycra is about 11% and the preferable percentage of Polyester is about 89%. However, other preferable percentages are about Polyester 95% and Lycra 5%; about Polyester 92% and Lycra 8%; about Polyester 90% and Lycra 10%; about Polyester 87% and Lycra 13%; about Polyester 85% and Lycra 15%; and about Polyester 82% and Lycra 18%. The Polyester and Lycra combination provide a material that is stretchable and has memory to return to its original unstretched length.

Figure 4:
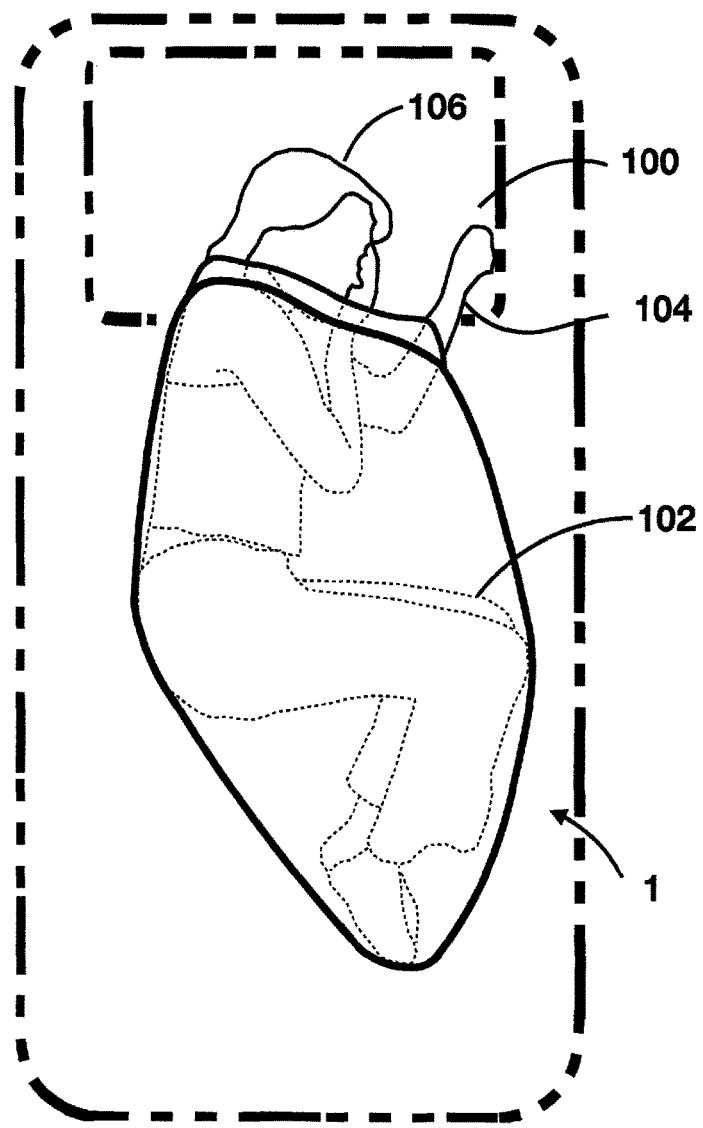
FIG. 4 is a top view of a user contained inside compression sleepwear in accordance with the present invention.

With reference to FIG. 4, a width and length of the body compression sleepwear 1 is smaller than a width and length of a user 100 to exert compressive force on the outer surface of the body of the user 100. The user 100 inserts their legs 102 and arms 104 through the entrance opening 28 and into the body pocket 22. A head 106 of a user 100 is not retained inside the neck portion. The user 100 may keep their arms 104 inside the body cavity 22 or extend a portion of one or two arms 104 outside the neck portion 12. It is preferable that the user 100 at least partially bend their legs 106 when in the body pocket 22, similar to a fetal position of a baby.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

I claim:

1. Body compression sleepwear comprising:
a first body side sheet having a first body portion and a first neck portion extending from said first body portion; and
a second body side sheet having a second body portion and a second neck portion extending from said second body portion, a perimeter of said first body portion is permanently attached to a perimeter of said second body portion such that a body pocket and a body portion are formed between said first and second body portions, said first and second neck portions are permanently attached to each other to form an entrance opening and a neck portion, said entrance opening communicates with said body pocket, said body portion and said neck portion are fabricated from a stretchable material with memory, said body compression sleepwear includes an unstretched configuration and a stretched configuration, a length and width of said body compression sleepwear is greater in said stretched configuration than in said unstretched configuration, wherein a length and width of the body compression sleepwear is configured to be less than a width and length of a user in said unstretched configuration, a width of the neck portion is configured to be less than a width of the user, and said entrance opening configured to receive a user's arms and legs therethough.

2. The body compression sleepwear of claim 1 wherein: said first neck portion is folded over to form a first double wall, said second neck portion is folded over to form a second double wall.

3. The body compression sleepwear of claim 1 wherein: a length of said neck portion is about 15 percent of a length of said body portion.

4. The body compression sleepwear of claim 1 wherein: a width of said neck portion is about 60 percent of a width of said body portion.

5. The body compression sleepwear of claim 1 wherein: said stretchable material is fabricated from a combination of Polyester and Lycra.

6. The body compression sleepwear of claim 1 wherein: said stretchable material is composed of about 89 percent Polyester and about 11 percent Lycra.

7. The body compression sleepwear of claim 1 wherein: opposing sides of said neck portion are parallel to each other.

8. Body compression sleepwear comprising:
a body portion includes a first body sheet and a second body sheet, a straight end is formed on the first and second body sheets, a perimeter of the first and second body sheets are permanently attached to each other to form a body pocket; and
a neck portion having a first neck sheet and a second neck sheet, opposing ends of said first and second neck sheet are permanently attached to each other to form an entrance opening, a bottom end of said first and second neck sheets are attached to said straight end of said first and second body sheets, said entrance opening communicates with said body pocket, said body portion and said neck portion are fabricated from a stretchable material with memory, said body compression sleepwear includes an unstretched configuration and a stretched configuration, a length and width of said body compression sleepwear is greater in said stretched configuration than in said unstretched configuration, wherein a length and width of the body compression sleepwear is configured to be less than a width and length of a user in said unstretched configuration, a width of the neck portion is configured to be less than a width of the user, and said entrance opening configured to receive a user's arms and legs therethough.

9. The body compression sleepwear of claim 8 wherein: a length of said neck portion is about 15 percent of a length of said body portion.

10. The body compression sleepwear of claim 8 wherein: a width of said neck portion is about 60 percent of a width of said body portion.

11. The body compression sleepwear of claim 8 wherein: said stretchable material is fabricated from a combination of Polyester and Lycra.

12. The body compression sleepwear of claim 8 wherein: said stretchable material is composed of about 89 percent Polyester and about 11 percent Lycra.

13. The body compression sleepwear of claim 8 wherein: opposing sides of said neck portion are parallel to each other.

14. Body compression sleepwear comprising:
a body portion includes a first body sheet and a second body sheet, a straight end is formed on the first and second body sheets, a perimeter of the first and second body sheets are permanently attached to each other to form a body pocket; and
a neck portion having a first neck sheet and a second neck sheet, said first neck sheet is folded over to form a first double wall, said second neck sheet is folded over to form a second double wall, opposing ends of said first and second neck sheet are permanently attached to each other to form an entrance opening, a bottom end of said first and second neck sheets are attached to said straight end of said first and second body sheets, said entrance opening communicates with said body pocket, said body portion and said neck portion are fabricated from a stretchable material with memory, said body compression sleepwear includes an unstretched configuration and a stretched configuration, a length and width of said body compression sleepwear is greater in said stretched configuration than in said unstretched configuration, wherein a length and width of the body compression sleepwear is configured to be less than a width and length of a user in said unstretched configuration, a width of the neck portion is configured to be less than a width of the user, and said entrance opening configured to receive a user's arms and legs therethough.

15. The body compression sleepwear of claim 14 wherein:
a length of said neck portion is about 15 percent of a length of said body portion.

16. The body compression sleepwear of claim 14 wherein:
a width of said neck portion is about 60 percent of a width of said body portion.

17. The body compression sleepwear of claim 14 wherein:
said stretchable material is fabricated from a combination of Polyester and Lycra.

18. The body compression sleepwear of claim 12 wherein:
said stretchable material is composed of about 89 percent Polyester and about 11 percent Lycra.

19. The body compression sleepwear of claim 14 wherein:
opposing sides of said neck portion are parallel to each other.

* * * * *